United States Patent [19]

Spivack

[11] 4,433,087
[45] Feb. 21, 1984

[54] ALKYLATED 2,2'-BIPHENYLENE PHOSPHONATES AND STABILIZED COMPOSITIONS

[75] Inventor: John D. Spivack, Spring Valley, N.Y.

[73] Assignee: Ciba-Geigy Corporation, Ardsley, N.Y.

[21] Appl. No.: 267,116

[22] Filed: May 26, 1981

Related U.S. Application Data

[63] Continuation of Ser. No. 75,289, Sep. 12, 1979, abandoned, which is a continuation of Ser. No. 964,407, Nov. 28, 1978, abandoned, which is a continuation of Ser. No. 866,749, Jan. 3, 1978, abandoned.

[51] Int. Cl.³ .......................... C08K 5/52; C07F 9/15
[52] U.S. Cl. ................................. 524/117; 260/936
[58] Field of Search ......................... 260/936; 524/117

[56] References Cited

U.S. PATENT DOCUMENTS 4,143,028  3/1979  Spivack ............................. 260/936
4,196,117  4/1980  Spivack ............................. 260/936

FOREIGN PATENT DOCUMENTS 2856801  7/1979  Fed. Rep. of Germany .

OTHER PUBLICATIONS

Mukmeneva et al., "Chemical Abstracts," vol. 82, (1975), 58628v and 140926z.

Primary Examiner—Anton H. Sutto
Attorney, Agent, or Firm—Harry Falber

[57] ABSTRACT

Alkylated 2,2'-biphenylene phosphonates are prepared by reacting alkylated 2,2'-biphenol with phosphoros trichloride in an organic solvent and then with a base such as sodium hydroxide. Said phosphonates are useful as stabilizers of organic polymers and lubricating oils, especially as stabilizers for polyolefins, polyesters, and polycarbonates.

3 Claims, No Drawings

ALKYLATED 2,2'-BIPHENYLENE PHOSPHONATES AND STABILIZED COMPOSITIONS

This is a continuation of application Ser. No. 75,289 filed on Sep. 12, 1979, now abandoned which in turn is a continuation of application Ser. No. 964,407, filed Nov. 28, 1978, (now abandoned), which in turn is a continuation of application Ser. No. 866,749, filed Jan. 3, 1978, (now abandoned).

BACKGROUND OF THE INVENTION

Organic polymeric materials such as plastics and resins and lubricating and mineral oil are subject to thermal, oxidative and photodegradation. A great variety of stabilizers are known in the art for stabilizing various substrates. Their effectiveness varies depending on the causes of degradation and the substrate stabilized. During the course of this work it was discovered that stabilizers that are very effective long term antioxidants are relatively poor process stabilizers which require stabilization of the substrate, against thermal degradation for a short time but at a relatively high temperature. Many stabilizers are relatively incompatible with the substrate which causes problems during the life of a product and lessens the stabilizer's effectiveness. Some stabilizers are either too volatile or thermally or hydrolytically unstable to be practical as commercial stabilizers.

The phosphonates of this invention possess an unusual combination of desirable properties as compared to the prior art phosphonates which makes these compounds particularly effective and useful as stabilizers. The prior art discloses unhindered 2,2'-biphenylenephenylphosphonates and 2,2'-methylene bis-(dialkylphenyl) phenylphosphonates, Chem. Abst. 82, 58628V (1975) and Chem. Abst. 82, 140926Z (1975) which are said to inhibit oxidative degradation and improve color stability of polyethylene. However, the phosphonates of this invention are much more effective, especially as process stabilizers of polyolefins and other substrates.

DETAILED DISCLOSURE

This invention is directed to alkylated 2,2'-biphenylene phosphonites and to polymeric and non-polymeric organic materials stabilized with said phosphonites. More specifically the phosphonites of this invention can be represented by the formula

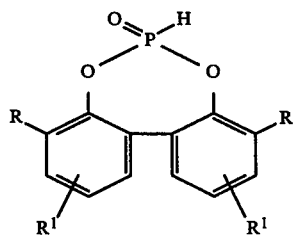

wherein
R is an alkyl group of 1 to 18 carbon atoms and
$R^1$ is hydrogen or an alkyl group of 1 to 18 carbon atoms.

The R groups are preferably straight-chain or branched alkyl with 1-8 carbon atoms, such as methyl, ethyl, n-propyl, iso-propyl, n-butyl, sec.-butyl, tert.-butyl, 2-ethylhexyl and n-octyl and tert-octyl. α-Branched alkyl radicals with 3-8 atoms are more preferred. The groups tert-butyl and tert-octyl are especially preferred. Also especially preferred is for the $R^1$ group to be in the para position to oxygen, particularly if $R^1$ is a tert.-alkyl.

Although $R^1$ can be hydrogen or alkyl of 1 to 18 carbons, preferably it is an alkyl group of 1 to 8 carbon atoms, either straight-chain or branched-chain. Especially preferred is tert-alkyl of 4 to 8 carbon atoms.

The alkylated 2,2'-biphenylene phosphonites of this invention can be prepared by reacting an alkylated 2,2'-biphenol with phosphorus trichloride in a solvent. The solvent is preferably aromatic, such as benzene, toluene, xylene and the like. The reaction can be carried out either in the absence or presence of a proton acceptor such as a tetiary amine, for example, triethylamine, pyridine, N,N-dimethylaniline, and the like. A reaction temperature from room temperature to the reflux temperature of the reaction may be employed. The resulting alkylated 2,2'-biphenylenephosphorochloridite is then hydrolyzed with an alkali hydroxide, such as sodium or potassium hydroxide to the desired product. Another method of preparing the compounds of this invention is to prepare first a phenolate ion by reacting an alkylated 2,2'-biphenol with an alkali metal hydroxide and then reacting the phenolate ion with phosphorus trichloride.

The compounds of this invention are effective light stabilizers and/or antioxidants in a wide range of organic polymers. Polymers which can be stabilized include:

1. Polymers which are derived from mono- or diolefins, e.g., polyethylene which can optionally be crosslinked, polypropylene, polyisobutylene, polymethylbutene-1, polymethylpentene-1, polyisoprene, polybutadiene.
2. Mixtures of the homopolymers cited under (1), for example mixtures of polypropylene and polyethylene, polypropylene and polybutene-1, polypropylene and polyisobutylene.
3. Copolymers of the monomers based on the homopolymers cited under (1), for example ethylene/propylene copolymers, propylene/butene-1 copolymers, propylene/isobutylene copolymers, ethylene/butene-1 copolymers as well as terpolymers of ethylene and propylene with a diene, for example hexadiene, dicyclopentadiene or ethylidene norbornene, and copolymers of a α-olefins, e.g., ethylene, with acrylic or methacrylic acid.
4. Polystyrene.
5. Copolymers of styrene and of a α-methylstyrene, for example styrene/butadiene copolymers, styrene/acrylonitrile copolymers, styrene/acrylonitrile/methylacrylate copolymers, styrene/acrylonitrile/acrylic ester copolymers, styrene/acrylonitrile copolymers modified with acrylic ester polymers to provide impact strength as well as block copolymers, e.g., styrene/butadiene/styrene block copolymers.
6. Graft copolymers of styrene, for example the graft polymer of styrene to polybutadiene, the graft polymer of styrene with acrylonitrile to polybutadiene as well as mixtures thereof with the copolymers cited under (5), commonly referred to as acrylonitrile/butadiene/styrene or ABS plastics.
7. Halogen-containing vinyl polymers, for example polyvinyl chloride, polyvinylidene chloride, polyvinyl fluoride, polychloroprene, chlorinated rubbers, vinyl chloride/vinylidene chloride copolymers, vinyl chloride/vinyl acetate copolymers, vinylidene chloride/vinyl acetate copolymers.

8. Polymers which are derived from α,β-unsaturated acids and derivatives thereof, polyacrylates and polymethacrylates, polyacrylic amides and polyacrylonitrile.
9. Polymers which are derived from unsaturated alcohols and amines and from the acyl derivatives thereof or acetals, for example polyvinyl alcohol, polyvinyl acetate, polyvinyl stearate, polyvinyl benzoate, polyvinyl maleate, polyvinyl butyral, polyallyl phthalate, polyallyl melamine and copolymers thereof with other vinyl compounds, for example ethylene/vinyl acetate copolymers.
10. Homopolymers and copolymers which are derived from epoxides, for example polyethylene oxide or the polymers which are derived from the bis-glycidyl ethers.
11. Polyacetals, for example polyoxymethylene, as well as polyoxymethylenes which contain ethylene oxide as comonomer.
12. Polyalkylene oxides, for example polyoxyethylene, polypropylene oxide or polyisobutylene oxide.
13. Polyphenylene oxides.
14. Polyurethanes and polyureas.
15. Polycarbonates.
16. Polysulphones.
17. Polyamides and copolyamides which are derived from diamines and dicarboxylic acids and/or from aminocarboxylic acids or the corresponding lactams, for example polyamide 6, polyamide 6/6, polyamide 6/10, polyamide 11, polyamide 12, poly-m-phenylene-isophthalamide.
18. Polyesters which are derived from dicarboxylic acids and dialcohols and/or from hydroxycarboxylic acids or the corresponding lactones, for example polyethylene glycol terephthalate, poly-1,4-dimethylol-cyclohexane terephthalate.
19. Cross-linked polymers which are derived from aldehydes on the one hand and from phenols, ureas and melamines on the other, for example phenol/-formaldehyde, urea/formaldehyde and melamine/-formaldehyde resins.
20. Alkyd resins, for example glycerol/phthalic acid resins and mixtures thereof with melamine/formaldehyde resins.
21. Saturated polyester resins which are derived from copolyesters of saturated and unsaturated dicarboxylic acids with polyhydric alcohols as well as from vinyl compounds as cross-linking agents and also the halogen-containing, flame-resistant modifications thereof.
22. Natural polymers, for example cellulose, rubber, as well as the chemically modified homologous derivatives thereof, for example cellulose acetates, cellulose propionates and cellulose butyrates and the cellulose ethers, for example methyl cellulose.

Compounds of this invention are particularly effective in stabilizing organic materials such as plastics, polymers, resins in addition to mineral and synthetic fluids such as lubricating oils, circulating oils, etc.

The compounds of this invention are particularly useful as stabilizers, especially for the protection of polyolefins, for instance, polyethylene, polypropylene, polyisobutylene, poly (butene-1), poly(pentene-1), poly(3-methylbutene-1) poly(4-methyl pentene-1), various ethylene-propylene copolymers and the like.

Other substrates in which the compounds of this invention are particularly useful are polystyrene, including impact polystyrene, ABS resin, SBR, isoprene, as well as natural rubber, polyesters including polyethylene terephthalate and polybutylene terephthalate, including copolymers. Also stabilized are polyurethanes, polycarbonates, polyamides such as nylon 6, 6/6 and the like as well as copolyamides and polysulfones.

The compounds of this invention may be used alone as the sole stabilizer having either mainly an antioxidant function or a light stabilizing function or the stabilizer may combine utility as an antioxidant and light stabilizer. The stabilizers may be used with phenolic antioxidants, lubricants such as calcium stearate, pigments, colorants or dyes, UV absorbers, light stabilizers such as hindered amines, metal deactivators, talc and other fillers, etc.

In general, the stabilizers of this invention are employed from about 0.01 to about 5% by weight of the stabilized composition, although this will vary with the particular substrate and application. An advantageous range is from about 0.05 to about 2%, and especially 0.1 to about 1%.

Compounds of this invention stabilize polymers especially during high temperature processing with relatively little change in color, even though the polymer may undergo a number of extrusions. Among the polymers in which this property is especially apparent are polypropylene, polyethylene, styrenics such as ABS, polyethylene- and polybutylene-tere-phthalates, polycarbonates, natural rubber, synthetic rubber such as SBR. While many compounds which have been used as process stabilizers are sufficiently effective as process stabilizers for polyolefins only in the presence of costabilizers such as phenolic antioxidants, compounds of this invention are effective in the absence of phenolic antioxidants. Many of the compounds of this invention combine process stabilizing properties with the ability to confer light stability on the polymer. This is particularly important for polymer fibers where processing temperatures are among the highest and where stability to actinic light is a prime requirement. A particularly important property for stabilizers which are trivalent phosphorus esters is their non-hygroscopicity and resistance to hydrolysis in the presence of moisture in the atmosphere during ambient storage. Hygroscopicity frequently results in difficulty in incorporating the process stabilizer uniformly into the polymer causing stickiness and blockage during compounding, while hydrolysis of the phosphorus ester stabilizers during storage frequently results in compounds which are less effective.

The stabilizers of formula I may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain various conventional additives, such as the following:

1. Antioxidants 1.1 Simple 2,6-dialkylphenols, such as, for example, 2,6-di-tert.-butyl-4-methylphenol, 2-tert.-butyl-4,6- dimethylphenol, 2,6-di-tert.-butyl-4-methoxymethylphenol and 2,6-dioctadecyl-4-methylphenol.

1.2 Derivatives of alkylated hydroquinones, such as, for example, 2,5-di-tert.-butyl-hydroquinone, 2,5-di-tert.-amylhydroquinone, 2,6-di-tert.-butyl-hydroquinone, 2,5-di-tert.-butyl-4-hydroxy-anisole, 3,5-di-tert.-butyl-4-hydroxy-anisole, tris-(3,5-di-tert.-butyl-4-hydroxyphenyl) phosphite, 3,5-di-tert.-butyl-4-hydroxyphenyl stearate and bis-(3,5-di-tert.-butyl-4-hydroxyphenyl) adipate.

1.3. Hydroxylated thiodiphenyl ethers, such as, for example, 2,2'-thio-bis-(6-tert.-butyl-4-methylphenol), 2,2'-thio-bis-(4-octylphenol), 4,4'-thio-bis-(6-tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxyphenyl) disulphide.

1.4. Alkylidene-bisphenols, such as, for example, 2,2'-methylene-bis-(6-tert.-butyl-4-methylphenol), 2,2'-methylene-bis-(6-tert.-butyl-4-ethylphenol), 4,4'-methylene-bis-(6-tert.-butyl-2-methylphenol), 4,4'-methylene-bis-(2,6-di-tert.-butylphenol), 2,6-di-(3-tert.-butyl-5-methyl-2-hydroxybenzyl)-4-methylphenol, 2,2'-methylene-bis-[4-methyl-6-(α-methylcyclohexyl)-phenol], 1,1-bis-(3,5-dimethyl-2-hydroxyphenyl)-butane, 1,1-bis-(5-tert.-butyl-4-hydroxy-2-methylphenyl)-butane, 2,2-bis-(3,5-di-tert.-butyl-4-hydroxyphenyl)-propane, 1,1,3-tris-(5-tert.-butyl-4-hydroxy-2-methylphenyl)-butane, 2,2-bis-(5-tert.-butyl-4-hydroxy-2-methylphenyl)-4-n-dodecylmercaptobutane, 1,1,5,5-tetra-(5-tert.-butyl-4-hydroxy-2-methylphenyl)-pentane and ethylene glycol bis-[3,3-(3'-tert.-butyl-4'-hydroxyphenyl)-butyrate].

1.5 O-, N- and S-benzyl compounds, such as, for example, 3,5,3',5'-tetra-tert.-butyl-4,4'-dihydroxydibenzyl ether, octadecyl 4-hydroxy-3,5-dimethylbenzyl-mercaptoacetate, tris-(3,5-di-tert.-butyl-4-hydroxybenzyl)-amine and bis-(4-tert.-butyl-3-hydroxy-2,6-dimethylbenzyl) dithioterephthalate.

1.6 Hydroxybenzylated malonates, such as, for example, dioctadecyl 2,2-bis-(3,5-di-tert.-butyl-2-hydroxybenzyl)-malonate, dioctadecyl 2-(3-tert.-butyl-4-hydroxy-5-methylbenzyl)-malonate, di-dodecylmercapto-ethyl 2,2-bis-(3,5-di-tert.-butyl-4-hydroxybenzyl)-malonate and di-[4-(1,1,3,3-tetramethylbutyl)phenyl] 2,2-bis-(3,5-di-tert.-butyl-4-hydroxybenzyl)-malonate.

1.7 Hydroxybenzyl-aromatic compounds, such as, for example, 1,3,5-tri-(3,5-di-tert.-butyl-4-hydroxybenzyl)-2,4,6-trimethylbenzene, 1,4-di-(3,5-di-tert.-butyl-4-hydroxybenzyl)-2,3,5,6-tetramethylbenzene and 2,4,6-tri-(3,5-di-tert.-butyl-4-hydroxybenzyl)-phenol.

1.8 s-Triazine compounds, such as, for example, 2,4-bis-octylmercapto-6-(3,5-di-tert.-butyl-4-hydroxyanilino)-s- triazine, 2-octylmercapto-4,6-bis-(3,5-di-tert.-butyl-4-hydroxyanilino)-s-triazine, 2-octylmercapto-4,6-bis-(3,5-di-tert.-butyl-4-hydroxyphenoxy)-s-triazine,2,4,6-tris-(3,5-di-tert.-butyl-4-hydroxyphenoxy)-s-triazine, 2,4,6-tris-(3,5-di-tert.-butyl-4-hydroxyphenylethyl)-s-triazine and 1,3,5-tris-(3,5-di-tert.-butyl-4-hydroxybenzyl) isocyanurate.

1.9 Amides of β-(3,5-di-tert.-butyl-4-hydroxyphenyl)-propionic acid, such as, for example, 1,3,5-tris-(3,5-di-tert.-butyl-4-hydroxyphenyl-propionyl)-hexahydro-s-triazine and N,N'-di-(3,5-di-tert.-butyl-4-hydroxyphenyl-propionyl)-hexamethylenediamine. N,N'-bis-β-(3,5-di-t-butyl-4-hydroxyphenyl)-propionyl-hydrazine.

1.10 Esters of β-(3,5-di-tert.-butyl-4-hydroxyphenyl)-propionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2,2,2]octane.

1.11 Esters of β-(5-tert.-butyl-4-hydroxy-3-methylphenyl)propionic acid with monohydric or polyhydric alcohols, such as, for example, with methanol, ethanol, octadecanol, 1,6-hexanediol, 1,9-nonanediol, ethylene glycol, 1,2-propanediol, di-ethylene glycol, thiodiethylene glycol, neopentylgylcol, pentaerythritol, 3-thia-undecanol, 3-thia-pentadecanol, trimethylhexanediol trimethylolethane, trimethylolpropane, tris-hydroxyethyl isocyanurate and 4-hydroxymethyl-1-phospha-2,6,7-trioxabicyclo[2,2,2]octane.

1.12 Esters of 3,5-di-tert.-butyl-4-hydroxyphenylacetic acid with monohydric or polyhydric alcohols, such as, for example, with methanol, ethanol, octandecanol, 1,6-hexanediol, 1,9-nonanediol, ethylene glycol, 1,2-propanediol, diethylene glycol, thiodiglycol, neopentylglycol, pentaerythritol, 3-thia-undecanol, 3-thia-pentadecanol, trimethylhexanediol, trimethyloleth-ane, trimethylolpropane, tris-hyroxyethyl isocyanurate and 4-hydroxymethyl-1-phospha-2,6,7-trioxabicyclo[2,2,2]octane, especially the tetra-bis ester of pentaerythritol.

1.13 Benzylphosphonates, such as, for example, dimethyl 3,5-di-tert.-butyl-4-hydroxybenzyl-phosphate, diethyl 3,5-di-tert.-butyl-4-hydroxybenzyl-phosphonate, dioctadecyl 3,5-di-tert.-butyl-4-hydroxybenzyl-phosphonate and dioctadecyl 5-tert.-butyl-4-hydroxy-3-methylbenzyl-phosphonate.

The following may be mentioned as examples of further additives that can be used together with the stabilizer of this invention and the antioxidant:

1. Aminoaryl derivatives, e.g. phenyl-1-naphthylamine, phenyl-2-naphthylamine, N,N'-di-phenyl-1-p-phenylenediamine, N,N'-di-2-naphthyl-p-phenylenediamine, N,N'-di-2-naphthyl-p-phenylenediamine, N,N'-di-rec.-butyl-p-phenylenediamine, 6-ethoxy-2,2,4-trimethyl- 1,2-dihydroquinoline, 6-dodecyl-2,2,4-trimethyl-1,2-dihydroquinoline, mono- and dioctyliminodibenzyl, polymerized 2,2,4-trimethyl1,2-dihydroquinoline. Octylated diphenylamine, nonylated diphenylamine, N-phenyl-N'-cyclohexyl-p-phenylenediamine, N-phenyl-N'-isopropyl-p-phenylenediamine, N,N'-di-sec.-octy-p-phenylenediamine, N-phenyl-N'-sec.-octyl-p-phenylenediamine, N,N'-di-(1,4-dimethylpentyl)-p-phenylenediamine, N,N'-dimethyl-N,N'-di-(sec.-octyl)-p-phenylenediamine, 2,6-dimethyl-4-methoxyaniline, 4-ethoxy-N-sec.-butylaniline, diphenylamineacetone condensation product, aldol-1-naphthylamine and phenothiazine.

Discoloration effects have to be taken into account when using the above antioxidants.

2. UV-Absorbers and light-stabilising agents 2.1 2-(2'-Nhdroxyphenyl)-benzotriazoles, e.g. the 5'-methyl-, 3',5'-di-tert.-butyl-, 5'-(1,1,3,3-tetramethylbutyl)-, 5-chloro-3',5'-di-tert.-butyl-, 5-chloro-3'-tert.-butyl-5'-methyl-, 3'-sec.-butyl-5'-tert.-butyl-, 3'-α-methylbenzyl-5'-methyl-, 3'-α-methylbenzyl-5'-methyl-5-chloro-, 4'-hydroxy-, 4'-methoxy-, 4'-octoxy-, 3',5'-di-tert.-amyl-, 3'-methyl-5'-carbomethoxyethyl- and 5-chloro-3',5'-di-tert.-amyl:derivative.

2.2. 2,4-bis-(2'-Hydroxyphenyl)-6-alkyl-s-triazines, e.g. the 6-ethyl-, 6-heptadecyl-, or 6-undecyl-derivative.

2.3. 2-Hydroxybenzophenones, e.g. the 4-hydroxy-, 4-methoxy-, 4-octoxy-, 4-decyloxy-, 4-dodecyloxy-, 4-benzyloxy-, 4,2',4'-trihydroxy- or 2'-hydroxy-4,4'-dimethoxy-derivative.

2.4. 1,3-bis-(2'-Hydroxybenzoyl)-benzenes, e.g. 1,3-bis-(2'-hydroxy-4'-hexyloxy-benzoyl)-benzene, 1,3-bis-(2'-hydroxy-4'-octyloxy-benzoyl)-benzene or 1,3-bis-(2'-hydroxy-4'-dodecyloxy-benzoyl)-benzene.

2.5. Esters of optionally substituted benzoic acids, e.g. phenylsalicylate, octylphenylsalicylate, dibenzoylresorcin, bis-(4-tert.-butylbenzoyl)-resorcin, benzoylresorcin, 3,5-di-tert.-butyl-4-hydroxybenzoic acid-2,4-di-tert.-butylphenyl ester or -octadecyl ester or -2-methyl-4,6-di-tert.-butyl ester.

2.6. Acrylates, e.g. α-cyano-β,β-diphenylacrylic acid-ethyl ester or -isooctyl ester, α-carbomethoxy-cinnamic acid methyl ester, α-cyano-β-methyl-p-methoxy-cinnamic acid methyl ester or -butyl ester or N-(β-carbomethoxyvinyl)-2-methyl-indoline.

2.7. Sterically hindered amines, e.g. 4-benzoyl-2,2,6,6-tetramethylpiperidine, 4-stearyloxy-2,2,6,6-tetramethylpiperidine, bis-(2,2,6,6-tetramethylpiperidyl)-sebacate or 3-n-octyl-7,7,9,9-tetramethyl-1,3,8-triazaspiro[4,5]decane-2,4-dione.

2.8. Oxalic acid diamides, e.g. 4,4'-di-octyloxy-oxanilide, 2,2'-di-octyloxy-5,5'-di-tert.-butyl-oxanilide, 2,2'-di-dodecyloxy-5,5'-di-tert.-butyl-oxanilide, 2-ethoxy-2'-ethyl-oxanilide, N,N'-bis-(3-dimethylaminopropyl)-axalamide, 2-ethoxy-5-tert.-butyl-2'-ethyl-oxanilide and the mixture thereof with 2-ethoxy-2'-ethyl- 5,4'-di-tert.-butyl-oxanilide, or mixtures of ortho- and para-methoxy as as well as of o- and p-ethoxy-disubstituted oxanilides.

3. Metal deactivators, e.g. oxanilide, isophthalic acid dihydramide, sebacic acid-bis-phenylhydriazide, bis-benzylidene-oxalic acid dihydrazide, N,N'-diacetaladipic acid dihydrazide, N,N'-bis-salicyloyloxalic acid dihydrazide, N,N'-bis-salicyloylhydrazine, N,N'-bis-(3,5-di-tert.-butyl-4-hydroxyphenylpropionyl)-hydroazine, N-salicyloyl-N'-salicylalhydrazine, 3-salicyloyol-amino-1,2,4-triazole or N,N'-bis-salicyloyl-thiopropionic acid dihydrazide.

4. Basic co-stabilisers, e.g. alkali metal salts and alkaline-earth metal salts of higher fatty acids, for example Ca-stearate, Zn-stearate, Mg-behenate, Na-ricinoleate or K-palmitate.

5. Nucleation agents, e.g. 4-tert.-butylbenzoic acid, adipic acid or diphenylacetic acid.

6. Phosphites, such as, for example, triphenyl phosphite, diphenylalkyl phosphites, phenyldialkyl phosphites, tri-(nonylphenyl) phosphite, trilauryl phosphite, trioctadecyl phosphite, 3,9-isodecyloxy-2,4,8,10-tetraoxa-3,9-diphospha[5,5]-undecane and tri-(4-hydroxy-3,5-di-tert.butylphenyl) phosphite.

Other additives that can be incorporated in the stabilized compositions are thiosynergists such as dilauryl-thiodiproprionate or distearylthiodipropionate lubricants such as stearyl alcohol fillers, carbon black, asbestos, kaolin, talc, glass fibers, pigments, optical brighteners, flameproofing agents and antistatic agents.

EXAMPLE 1

Preparation of
(4,4',6,6'-tetra-tert.-butyl-2,2'-biphenylene)
Phosphonate 14.53 grams of 46.3% aqueous potassium hydroxide was heated at reflux together with 24.6 grams of 4,4',6,6'-tetra-tert.-butyl-2,2'-biphenol dissolved in 400 ml of toluene and the water removed by azeotropic distillation.

8.22 grams of phosphorus trichloride was added over 10 minutes to the cooled pasty reaction mixture at a temperature of 10 to 25° C. The reaction mixture was first stirred at 27° C. for 20 hours and then at 85°–90° C. for 12 hours. The reaction mixture was cooled to room temperature, freed of insoluble solid by filtration, the filtrate being successively washed with 3 N aqueous hydrogen chloride, water and finally with saturated sodium bicarbonate solution until neutral. After drying over anhydrous sodium sulfate, the solvent was removed by distillation at reduced pressures and the isolated residue successively triturated with toluene and crystallized from n-heptane to give a white crystalline solid, m.p. 225°–227°.

EXAMPLE 2

Preparation of
(4,4',6,6'-tetra-tert.-butyl-2,2'-biphenylene)
phosphorochloridite 45.21 grams of phosphorus trichloride in 50 ml of toluene was added dropwise over 85 minutes to a solution of 123.0 grams of 4,4',6,6'-tetra-tert.-butyl-2,2'-biphenol and 60.6 grams of triethylamime in about 60 ml of toleune and stirred at room temperature overnight (about 20 hours). The reaction product was filtered free of triethylamine hydrochloride, the desired product being isolated by removal of the solvent at reduced pressure to yield a solid m.p. 168°–174°.

EXAMPLE 2(a)

Preparation of
(6,6'-di-t-butyl-4,4'-dimethyl-2,2'-biphenylene)
phosphorochloridite The above compound was made according to the procedure of Example 2 by substituting 6,6'-di-t-butyl-4,4'-dimethylphenol for 4,4',6,6'-tetra-t-butyl-2,2'-biphenol. The product was a crystalline solid.

EXAMPLE 3

Preparation of 6,6'-Di-tert.-butyl-4,4'-Dimethyl-0,0'-Biphenylene phosphonate

A solution of 15 grams of the phosphorochlorodite of Example 2(a) in 140 ml. of toluene was stirred with 17.5 ml. of 2 N aqueous sodium hydroxide at 24° to 25° C. for three hours. The organic phase was washed successively with water, in aqueous sodium hydroxide and water, and finally dried over anhydrous sodium sulfate. After removal of the solvent by distillation, the isolated residue was dissolved in a warm mixture of 180 ml. of heptane and 40 ml. of ethyl acetate, clarified by filtration and allowed to crystallize yielding the product as white crystals. After crystallization once again the white crystals melted at 209°–211° C.

Following the above described procedure the compounds as described in the table below are prepared.

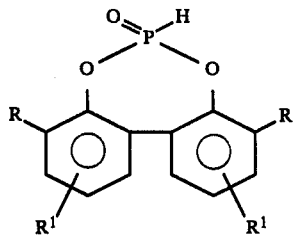

| Ex. No. | R | R¹ |
|---|---|---|
| 4 | tert-$C_5H_{11}$— | 4-tert-$C_5H_{11}$ |
| 5 | tert-$C_8H_{17}$— | 4-tert-$C_8H_{17}$ |
| 6 | $CH_3$— | 4-$CH_3$— |
| 7 | $(CH_3)_2CH$— | 4-$(CH_3)_2CH$— |
| 8 | $(CH_3)_3C$— | 4-$C_{18}H_{37}$— |
| 9 | $(CH_3)_3C$— | 3-$CH_3$— |

EXAMPLE 10

Stabilization of Polyethylene Terephthalate

1% of the compound of Example 1 was added to molten polyethylene terephthalate at 270° C. while stirring under a nitrogen atmosphere. After cooling the resulting formulated polymer was ground with solid carbon dioxide until the particle size was less than 100 microns in diameter. The temperature at which the onset of oxidation took place was determined as follows:

About 1 milligram of the polyester powder, as prepared above, was charged into the chamber of the Perkin-Elmer Differential Scanning Calorimeter and heated under nitrogen until a temperature of 225° C. was reached. The nitrogen flow was stopped and oxygen was introduced at a rate of 15 ml per minute while heating at a rate of 1 degree per minute until the oxidation exotherm was recorded. The oxidation temperature of the formulated powder was thus determined to be 258° while the base polyester powder without said compound was 246°. The higher oxidation temperature provided by said compound clearly shows the marked improvement in the inhibition of oxidation. The color of the polyester containing said stabilizer was also improved compared to that without additive.

EXAMPLE 11

Stabilization of Polycarbonate

A polycarbonate (Dow XP 5335) was formulated by mixing the base resin in a Waring Blender with 0.1% of the compound of Example 1, the base resin also containing 0.1% of octadecyl B(3.5-di-tert-butyl-4-hydroxyphenyl)propionate (Antioxidant A). The formulated resin was compression molded, cut into chips and charged into the melt index apparatus. After maintaining at 350° C. for 30 minutes a sample was removed compressed into plaques and examined for color. The sample containing the compound of Example 1 and Antioxidant A was much lighter in color than that containing Antioxidant A alone.

EXAMPLE 12

Color Improvement of Polypropylene During Multiple Extrusion at 500° F.

| | Base Formulation: | |
|---|---|---|
| (a) | Polypropylene (Profax 6801) | 100 |
| | Calcium stearate | 0.10 |
| (b) | Polypropylene (Profax 6801) | 100 |
| | Calcium stearate | 0.10 |
| | Antioxidant B pentaerithritol tetrakis-[3-(3',5'-t-butyl-4'-hydroxyphenyl)propionate] | 0.10 |

Stabilizers are solvent blended as solutions in methylene chloride onto base formulations (a) or (b) and, after removal of the solvent by evaporation at reduced pressure, the resin was extruded using the following extruder conditions:

| | Temp. (°F.) |
|---|---|
| Cylinder #1 | 450 |
| Cylinder #2 | 475 |
| Cylinder #3 | 500 |
| Die #1 | 500 |
| Die #2 | 500 |
| RPM | 100 |

During extrusion, the internal extruder pressure was determined using a pressure transducer. After each of the first, third and fifth extrusions, resin pellets were compression molded into 125 mil thick plaques at 380° F. and speciment yellowness index (Y.I.) determined according to ASTM D1925-63T.

TABLE II

COLOR IMPROVEMENT OF POLYPROPYLENE AT 500° F. DURING MULTIPLE EXTRUSION

Base Formulation: Polypropylene (Profax 6801) 100  
Calcium Stearate 0.1

| Additive | Conc. % | Transducer Pressure (psi) After Extrusion | | | YI Color After Extrusion | | |
|---|---|---|---|---|---|---|---|
| | | 1 | 3 | 5 | 1 | 3 | 5 |
| None (Base Formulation only) | — | 1020 | 790 | 640 | 5.3 | 7.4 | 9.3 |
| Antioxidant B | 0.10 | 1130 | 980 | 870 | 9.0 | 12.2 | 14.7 |
| 0.1% Antioxidant B + Compd. Ex. 3 | 0.05 | 1180 | 1015 | 885 | 6.8 | 8.1 | 9.3 |

EXAMPLE 13

Stabilization of Acrylonitrile - Butadiene - Styrene (ABS)

ABS resin was made by heating a base formulation shown below for 7.5 hours at 80° C. and identified as resin (a).

The base formulation from which resin (a) was made had the following composition:

| Butadiene | 10 |
|---|---|
| Acrylonitrile | 24 |
| Styrene | 65.8 |
| 2,2'-azobisiobutylonitrile | 0.1 |
| | 99.9 |

In a similar manner resin (b) was made containing in addition to the above base formulaton 9.25% of the compound of Example 3.

The oxidation temperature of each of the resins was determined by Differential Scanning Calorimetry employing the following procedure:

10 mg was charged to the DSC pan and heated from ambient temperature at a rate of 20° C./minute in an oxygen stream flowing at the rate of 250 ml/minute. The temperature at which an exotherm was observed for each of the resins was recorded.

The results show that ABS containing the compound of Example 3 is more stable than the resin without the additive.

What is claimed is:

1. A composition comprising an ethylene or propylene homopolymer or copolymer stabilized against oxidative and thermal degradation by the presence therein of an effective stabilizing amount of (4,4',6,6'-tetra-tert-butyl-2,2'-biphenyl) phosphonate or (4,4'-dimethyl-6,6'-di-tert-butyl-2,2'-biphenylene) phosphonate.

2. The compound which is (4,4',6,6'-tetra-tert.-butyl-2,2'-biphenylene) phosphonate.

3. The compound which is (4,4'-dimethyl-6,6'-di-tert-butyl-2,2'-biphenylene) phosphonate.

* * * * *